(12) United States Patent
Scampoli (10) Patent No.: US 11,116,422 B2
(45) Date of Patent: Sep. 14, 2021

(54) SAMPLE CELLS FOR RESPIRED GAS SAMPLING AND METHODS OF MANUFACTURING SAME

(71) Applicant: KONINKLIJKE PHILIPS N.V., Eindhoven (NL)

(72) Inventor: David Scampoli, South Glastonbury, CT (US)

(73) Assignee: Koninklijke Philips N.V., Eindhoven (NL)

( * ) Notice: Subject to any disclaimer, the term of this patent is extended or adjusted under 35 U.S.C. 154(b) by 510 days.

(21) Appl. No.: 16/064,639

(22) PCT Filed: Dec. 12, 2016

(86) PCT No.: PCT/IB2016/057522
§ 371 (c)(1),
(2) Date: Jun. 21, 2018

(87) PCT Pub. No.: WO2017/109631
PCT Pub. Date: Jun. 29, 2017

(65) Prior Publication Data
US 2019/0000351 A1    Jan. 3, 2019

Related U.S. Application Data (60) Provisional application No. 62/270,059, filed on Dec. 21, 2015.

(51) Int. Cl.
*A61B 5/097*    (2006.01)
*A61B 5/083*    (2006.01)
(Continued)

(52) U.S. Cl.
CPC ............ *A61B 5/097* (2013.01); *A61B 5/0836* (2013.01); *B29C 45/0053* (2013.01);
(Continued)

(58) Field of Classification Search
None
See application file for complete search history.

(56) References Cited

U.S. PATENT DOCUMENTS 4,859,859 A    8/1989  Knodle et al.
5,131,387 A *  7/1992  French ................... A61B 5/097
                                                    128/205.12
(Continued)

FOREIGN PATENT DOCUMENTS

WO    WO-2014027290 A1 *  2/2014  ............. A61B 5/097

*Primary Examiner* — Etsub D Berhanu
(74) *Attorney, Agent, or Firm* — Daniel H. Brean (57) ABSTRACT

A sample cell (10) for a respired gas sensor has a single-piece injection molded main body (40) defining a gas flow path including an optical sampling bore (42), a gas inlet lumen (50) connected with the inlet end (44) of the optical sampling bore, and a gas outlet lumen (52) connected with the outlet end (46) of the optical sampling bore. The gas flow path includes at least two curved walls (100, 102, 104, 106). The sample cell may be manufactured by assembling mold pins (120, 122, 124, 126, 128) for defining the gas flow path wherein at least two mold pins (122, 124) have curved surfaces for defining the at least two curved walls of the gas flow path, and injection molding the single piece injection molded main body including removing the mold pins after defining the gas flow path including the at least two curved walls.

15 Claims, 9 Drawing Sheets

(51) Int. Cl.
*G01N 21/05* (2006.01)
*B29C 45/26* (2006.01)
*B29C 45/00* (2006.01)
*G01N 21/3504* (2014.01)
*A61B 5/08* (2006.01)
*A61M 16/08* (2006.01)
*B29C 45/33* (2006.01)
*A61M 16/00* (2006.01)
*G01N 21/85* (2006.01)
*B29L 31/00* (2006.01)

(52) U.S. Cl.
CPC ........ *B29C 45/261* (2013.01); *B29C 45/2628* (2013.01); *G01N 21/05* (2013.01); *A61B 5/082* (2013.01); *A61B 2560/0443* (2013.01); *A61B 2562/12* (2013.01); *A61M 16/085* (2014.02); *A61M 2016/0027* (2013.01); *A61M 2016/0042* (2013.01); *A61M 2230/202* (2013.01); *B29C 45/33* (2013.01); *B29L 2031/752* (2013.01); *G01N 21/3504* (2013.01); *G01N 2021/8578* (2013.01)

(56) References Cited

U.S. PATENT DOCUMENTS

| | | | |
|---|---|---|---|
| 5,282,473 A * | 2/1994 | Braig | A61B 5/083 |
| | | | 250/343 |
| 5,616,923 A * | 4/1997 | Rich | G01N 21/0303 |
| | | | 250/338.5 |
| 5,693,944 A | 12/1997 | Rich | |
| 6,095,986 A * | 8/2000 | Braig | A61B 5/097 |
| | | | 128/204.23 |
| 6,468,222 B1 * | 10/2002 | Mault | A61B 5/0833 |
| | | | 600/529 |
| 7,335,164 B2 | 2/2008 | Blazewicz et al. | |
| 7,341,563 B2 | 3/2008 | Fudge et al. | |
| 7,556,039 B1 * | 7/2009 | Pierry | A61B 5/0836 |
| | | | 128/204.18 |
| 9,855,010 B2 | 1/2018 | Jaffe | |
| 2003/0191405 A1 | 10/2003 | Rich et al. | |
| 2004/0065835 A1 | 4/2004 | Rich et al. | |
| 2006/0251903 A1 * | 11/2006 | Eckerbom | G01N 21/0303 |
| | | | 428/423.7 |

\* cited by examiner

Section S-S
FIG. 5

Section S-S
FIG. 6

SAMPLE CELLS FOR RESPIRED GAS SAMPLING AND METHODS OF MANUFACTURING SAME

This application is a national stage application under 35 U.S.C. § 371 of International Application No. PCT/IB2016/057522 filed on Dec. 12, 2016 and published in the English language on Jun. 29, 2017 as International Publication No. WO 2017/109631, which claims priority to U.S. Patent Application No. 62/270,059 filed on Dec. 21, 2015, the entire disclosures of which are incorporated herein by reference.

FIELD

The following relates generally to the capnography arts, respired gas sampling arts, and to sample cells for use in such devices and to manufacturing methods for such sample cells, and to related arts.

BACKGROUND

Capnography is the monitoring of the concentration or partial pressure of carbon dioxide ($CO_2$) in respiratory gases. A known capnograph device is the Respironics® LoFlo® Sidestream $CO_2$ sensor available from Koninklijke Philips N.V., Eindhoven, the Netherlands, which uses a non-dispersive infrared (NDIR) single beam optical measurement technique to measure $CO_2$ in respiratory gas samples via a nasal cannula or other patient accessory. The LoFlo® $CO_2$ sensor includes a pump for drawing respiratory gas into a sample cell. A feature of the LoFlo® $CO_2$ sensor is the use of a disposable sample cell that is preferably replaced for each patient. This has advantages including avoiding contamination of the optical windows and flow path over time when the sample cell is re-used. In other capnograph devices, the sample cell is a non-disposable component which hence is prone to accumulating contamination on the optical windows and/or respiratory gas flow path.

The following discloses a new and improved systems and methods that address the above referenced issues, and others.

SUMMARY

In one disclosed aspect, a sample cell for a respired gas sensor is disclosed. The sample cell comprises: a single-piece injection molded main body defining a gas flow path including (i) an optical sampling bore with opposite inlet and outlet ends, (ii) a gas inlet lumen connected with the inlet end of the optical sampling bore, and (iii) a gas outlet lumen connected with the outlet end of the optical sampling bore; an inlet optical window attached to the single-piece injection molded main body and covering the inlet end of the optical sampling bore; and an outlet optical window attached to the single-piece injection molded main body and covering the outlet end of the optical sampling bore.

In another disclosed aspect, a sample cell for a respired gas sensor is disclosed. The sample cell comprises: a main body defining a gas flow path including (i) an optical sampling bore with opposite inlet and outlet ends, (ii) a gas inlet lumen connected with the inlet end of the optical sampling bore, and (iii) a gas outlet lumen connected with the outlet end of the optical sampling bore; an inlet optical window attached to the main body and covering the inlet end of the optical sampling bore; and an outlet optical window attached to the main body and covering the outlet end of the optical sampling bore; wherein the connection of the gas inlet lumen and the inlet end of the optical sampling bore includes at least one curved wall. In some embodiments, the connection of the gas outlet lumen and the outlet end of the optical sampling bore also includes at least one curved wall.

In another disclosed aspect, a method is disclosed of manufacturing a sample cell for a respired gas sensor having a single piece injection molded main body defining a gas flow path including (i) an optical sampling bore with opposite inlet and outlet ends, (ii) a gas inlet lumen connected with the inlet end of the optical sampling bore, and (iii) a gas outlet lumen connected with the outlet end of the optical sampling bore, wherein the gas flow path includes at least two curved walls. The method comprises: assembling mold pins for defining the gas flow path wherein at least two mold pins have curved surfaces for defining the at least two curved walls of the gas flow path; and injection molding the single piece injection molded main body including removing the mold pins after the mold pins have defined the gas flow path including the at least two curved walls.

One advantage resides in providing more accurate $CO_2$ measurements by improved respiratory gas flow through the sample cell.

Another advantage resides in providing $CO_2$ measurements with reduced time latencies and/or memory effects by improved respiratory gas flow through the sample cell.

Another advantage resides in providing a disposable or non-disposable respiratory gas sample cell with reduced manufacturing cost and simplified assembly.

Another advantage resides in providing a disposable respiratory gas sample cell with improved handling characteristics.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIGS. 3(*a*)-3(*g*) show multiple views of the single-piece injection molded main body of the sample cell of FIGS. 1 and 2.

DETAILED DESCRIPTION

Disclosed herein are improved sample cells for a capnography device or other respiratory gas sampling device.

Figure 1:
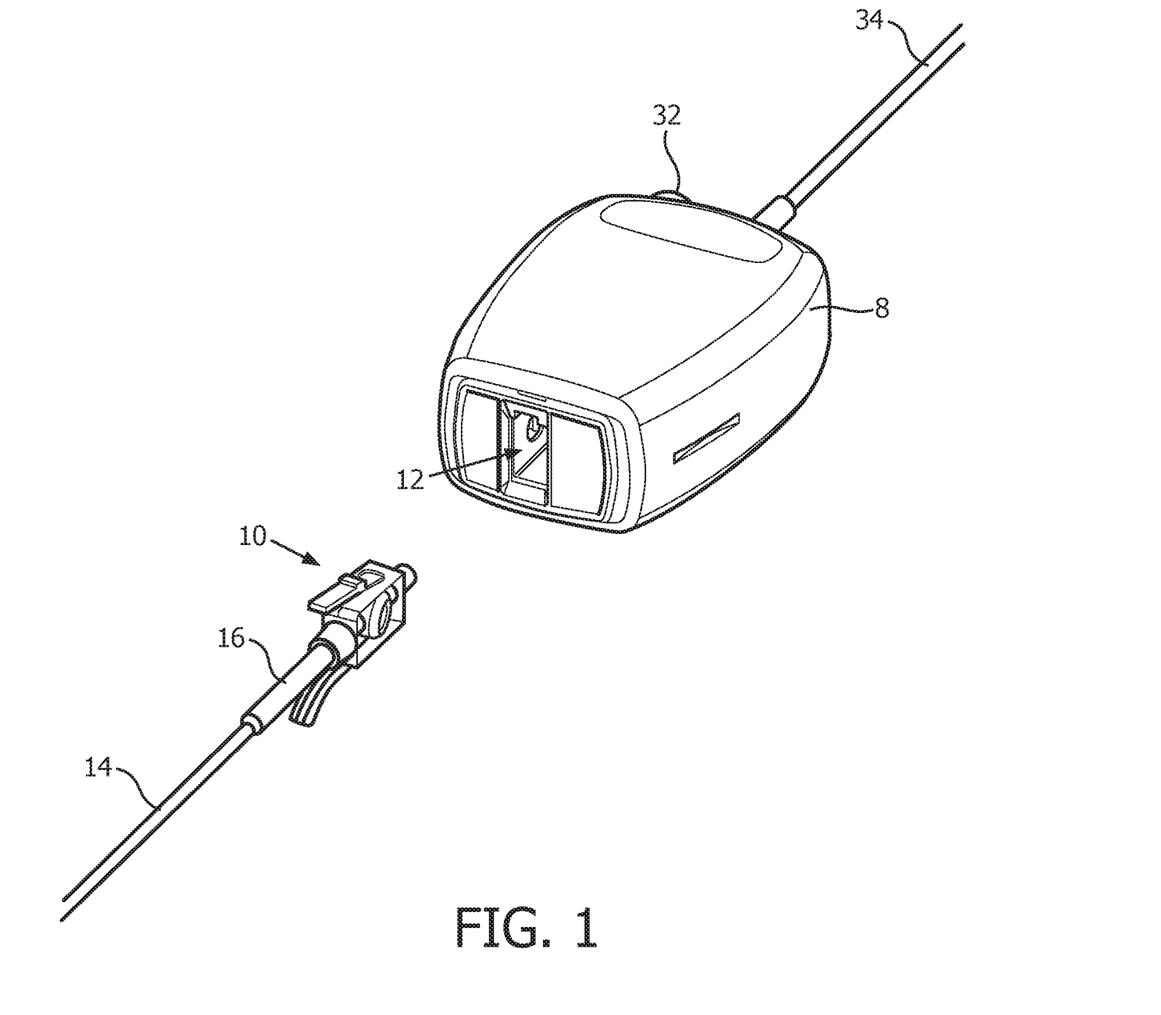
FIGS. 1 and 2 show a capnography device and a disposable sample cell before insertion into the capnograph device (FIG. 1) and after inserting the sample cell into the capnograph device (FIG. 2).
Figure 2:
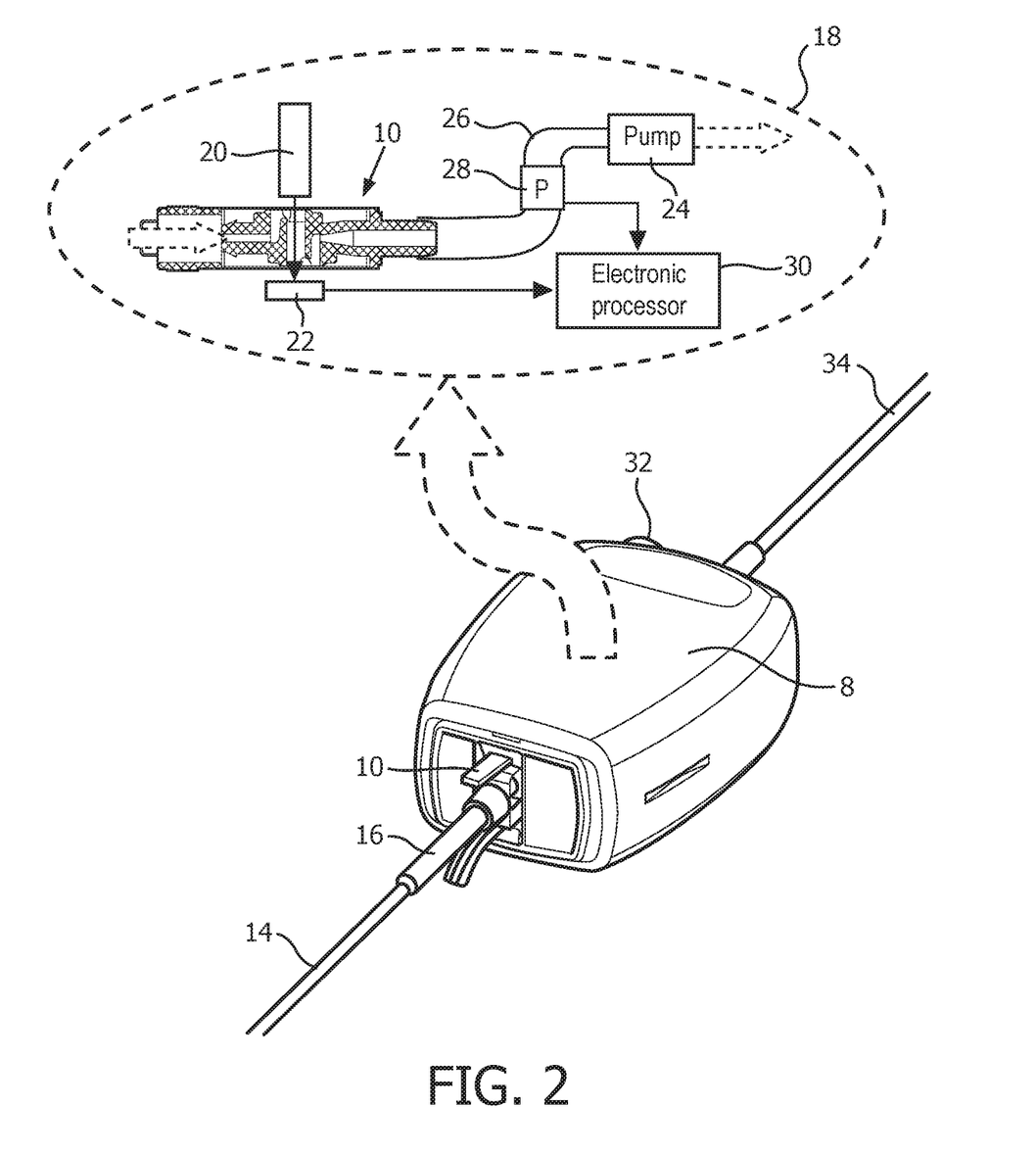

With reference to FIGS. 1 and 2, a capnography device is shown. The capnography device is a device for sampling carbon dioxide ($CO_2$) concentration or partial pressure in respired gas, and may alternatively be referred to as a $CO_2$ sensor device. As diagrammatically shown in FIG. 2, the capnography device includes a sampling bench 8 and a detachable sample cell 10 that inserts into a receptacle 12 of the sampling bench 8. FIG. 1 shows the disposable sample cell 10 before insertion into the receptacle 12 of the sampling bench 8, while FIG. 2 shows the assembly after the sample cell 10 is inserted into the sampling bench 8. The sample cell 10 is connected with an inlet air hose 14 via an intermediary water trap filter 16. The end of the inlet air hose 14 distal from its connection to the sample cell 10 is suitably connected to a patient accessory such as a nasal cannula or an in-line patient accessory coupling into a respirator line (patient accessory not shown) from which respired gas is drawn for sampling in the sidestream arrangement. The illustrative sample cell 10 is advantageously detachable and is preferably replaced at least between successive patients, so as to reduce buildup of contamination. While the illustrative sample cell 10 is detachable, in other embodiments it is contemplated for the sample cell to be a permanently installed component of the sampling bench.

With particular reference to FIG. 2, an inset 18 shows a cross-sectional view of the sample cell 10 from just downstream of the water trap filter 16, along with selected internal components of the sampling bench 8. As shown in inset 18, the sampling bench 8 houses an optical $CO_2$ sensing assembly comprising a laser or other light source 20 and a light detector 22. The illustrative sampling bench 8 is a sidestream sampling bench that draws (i.e. "samples") respired gas flow from the inlet air hose 14 through the sample cell 10 using a pump 24 that connects with an outlet end of the sample cell 10 via internal air tubing 26. The air flow system may also include an illustrative air pressure sensor 28, an air flow sensor (not shown), or other diagnostic sensor(s).

The illustrative sampling bench 8 further includes an on-board electronic data processing component 30, for example a microprocessor or microcontroller. The processing component 30 may be programmed to perform one or more self-diagnostic algorithms, for example, to detect if the unit is not connected with a patient based on the pressure reading output by the pressure sensor 28 and/or an air flow reading measured by an air flow sensor. The processing component 30 may additionally or alternatively be programmed to output respired air component information, for example $CO_2$ partial pressure or concentration as appropriate for the illustrative capnography device. This processing may include converting measured optical transmission from the infrared emitting device 20 to the sensor 22 into [$CO_2$] concentration, optionally with compensation such as for the barometric pressure, known $FiO_2$ level (for a patient receiving supplemental oxygen), or so forth. The respired carbon dioxide data may be output as a waveform, e.g. [$CO_2$] samples acquired at a sampling rate, and/or may be output in post-acquisition processed form, for example performing an end-tidal $CO_2$ ($etCO_2$) calculation algorithm comprising (1) detecting breath cycles from air pressure and/or flow versus time data acquired by the sensor(s) 28 and/or from the [$CO_2$] waveform, (2) detecting the peak $CO_2$ level for each breath which usually occurs in the end-tidal phase, and (3) optional filtering or other processing of the per-breath $etCO_2$ values for example averaging over N breaths to suppress noise. It will be appreciated that in various embodiments the processing performed on-board (that is, by the electronic processor 30 of the sampling bench 8) versus off-board can be varied. For example, in some embodiments the on-board electronic processor 30 outputs only the [$CO_2$] waveform and a bedside patient monitor (not shown) receives this waveform and computes the $etCO_2$. It is also contemplated to omit the electronic processor 30 entirely, e.g. outputting optical transmission measurement samples acquired by the optical detector 22 which are then converted to a [$CO_2$] waveform by a bedside monitor or other external device.

The respired gas flow output from the pump 24 may be vented directly to the ambient atmosphere. Alternatively, if the patient or other monitored subject is receiving an inhaled medication that should not be vented into the ambient atmosphere, then the gas flow output from the pump 24 may be output to a discharge air hose (not shown) via a suitable outlet air hose coupling 32. The illustrative sidestream sampling bench 8 further includes an electrical cable 34 which may, for example, carry: electrical power for driving components such as the light source 20 and the electronic processor 30; and one or more data lines carrying information such as the $CO_2$ data, self-diagnostic data, or so forth. In some embodiments, it is contemplated for the $CO_2$ data and/or self-diagnostic data to be output wirelessly, e.g. via a Bluetooth® or Zigbee® wireless communication link (not shown).

By way of non-limiting illustrative example, in some embodiments it is contemplated for the sampling bench 8 to be the sampling bench component of the Respironics® LoFlo® Sidestream $CO_2$ sensor (available from Koninklijke Philips N.V., Eindhoven, the Netherlands). This sampling bench uses a non-dispersive infrared (NDIR) single beam optical measurement technique to measure $CO_2$, and includes a pump for drawing respiratory gas into a sample cell. The Respironics® LoFlo® Sidestream $CO_2$ sensor includes a receptacle for receiving a detachable sample cell, and various embodiments of the illustrative detachable sample cell 10 disclosed herein may be employed in conjunction with this commercially available sampling bench.

It will be further appreciated that the disclosed sample cell embodiments may be employed in conjunction with other types of respiratory gas sensors that are designed to sense other respired gas components such as oxygen partial pressure or concentration, and may advantageously employ the disposable (as illustrated) or non-disposable sample cell 10.

Figure 3:
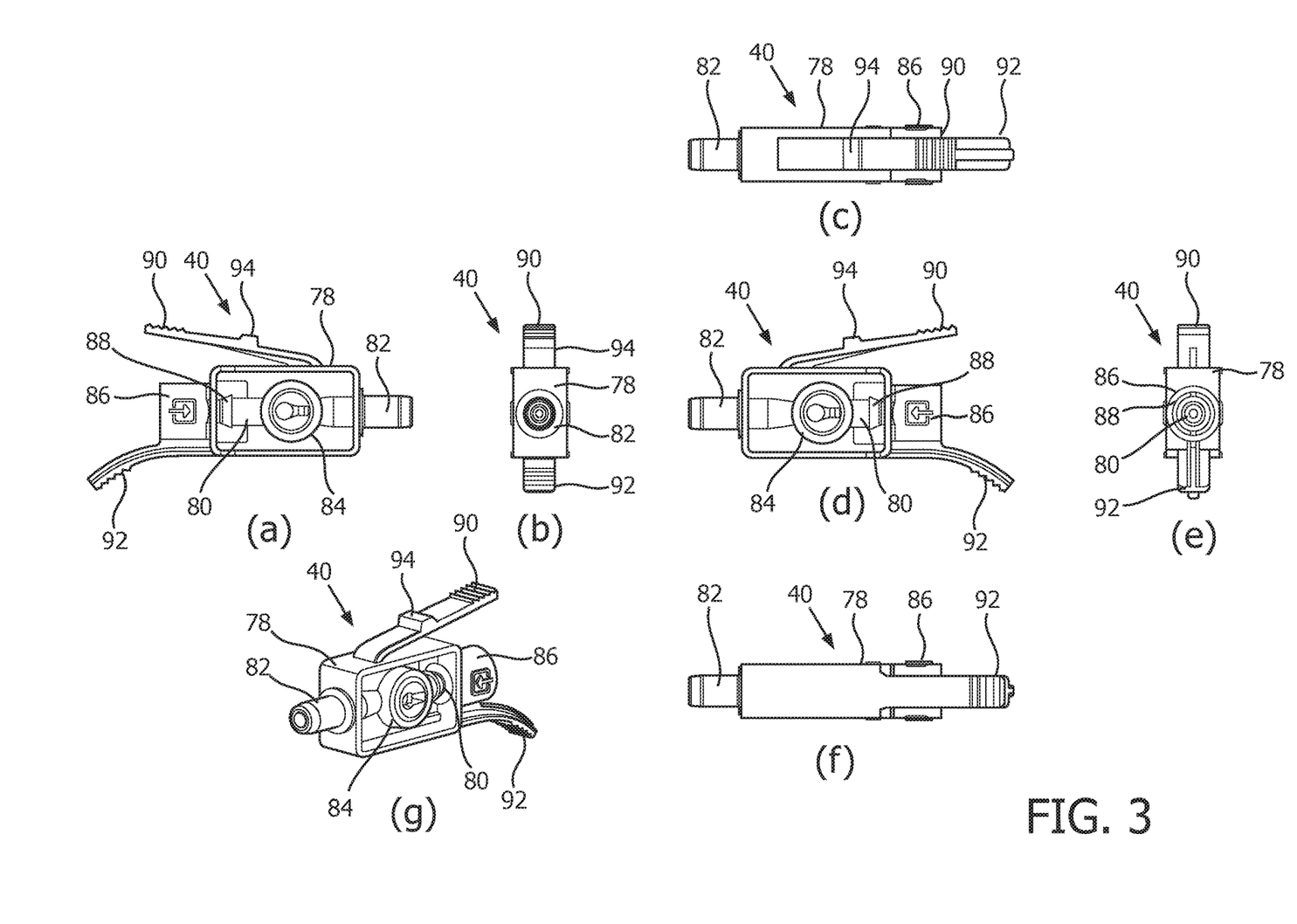
Figure 4:
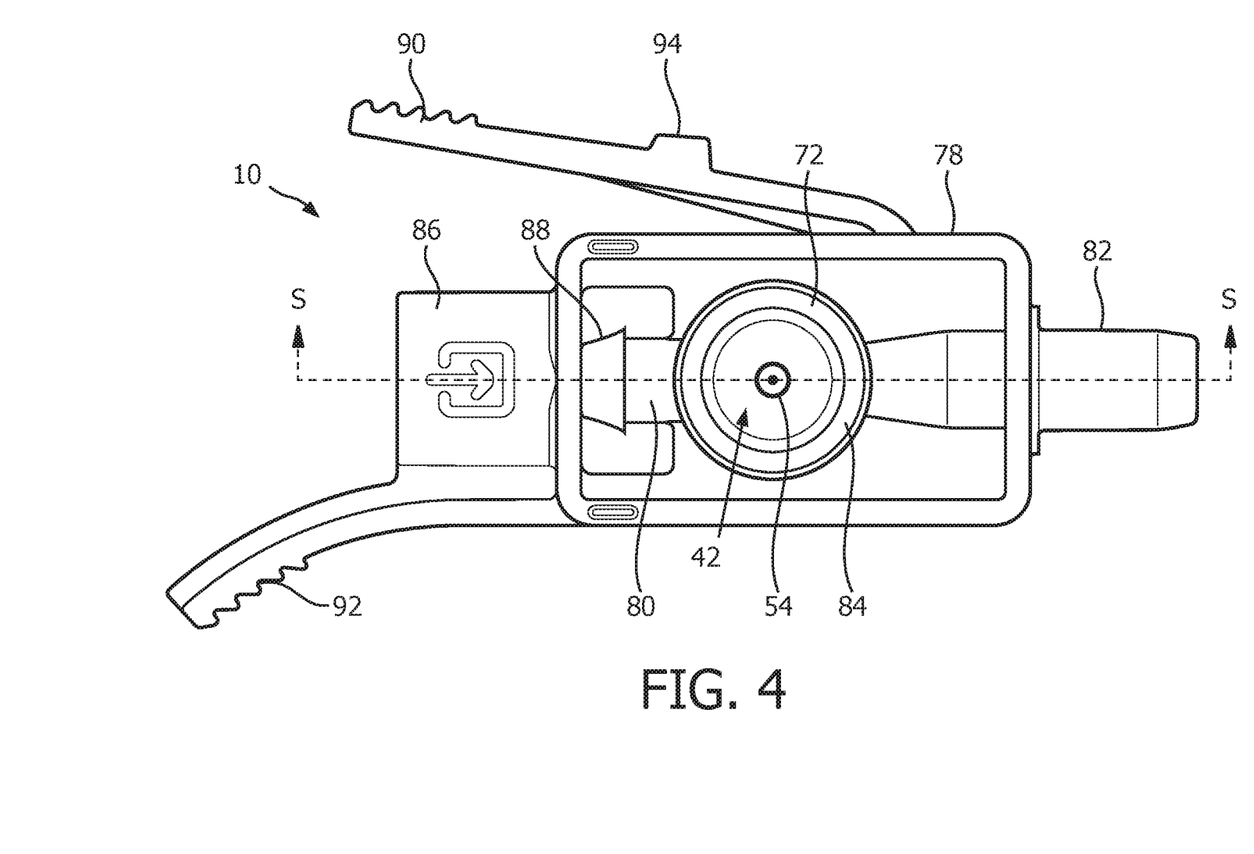
FIG. 4 shows a side view of the sample cell of FIGS. 1 and 2 with a Section S-S line indicated.
Figure 5:
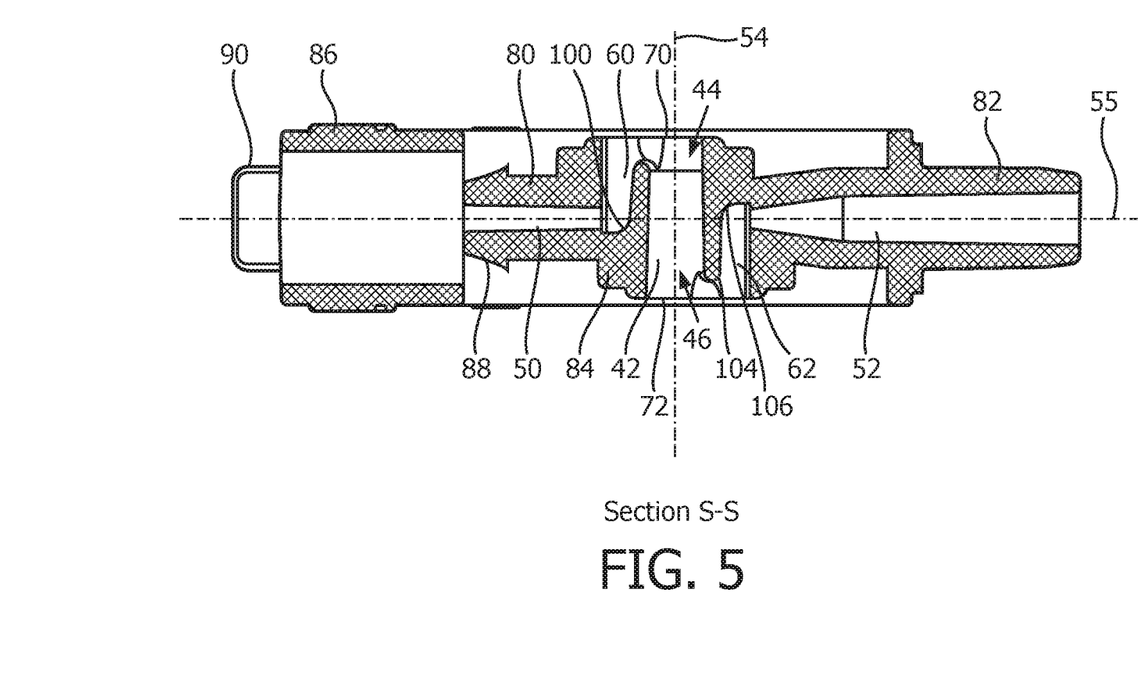
FIG. 5 shows Section S-S along the section line indicated in FIG. 4.
Figure 6:
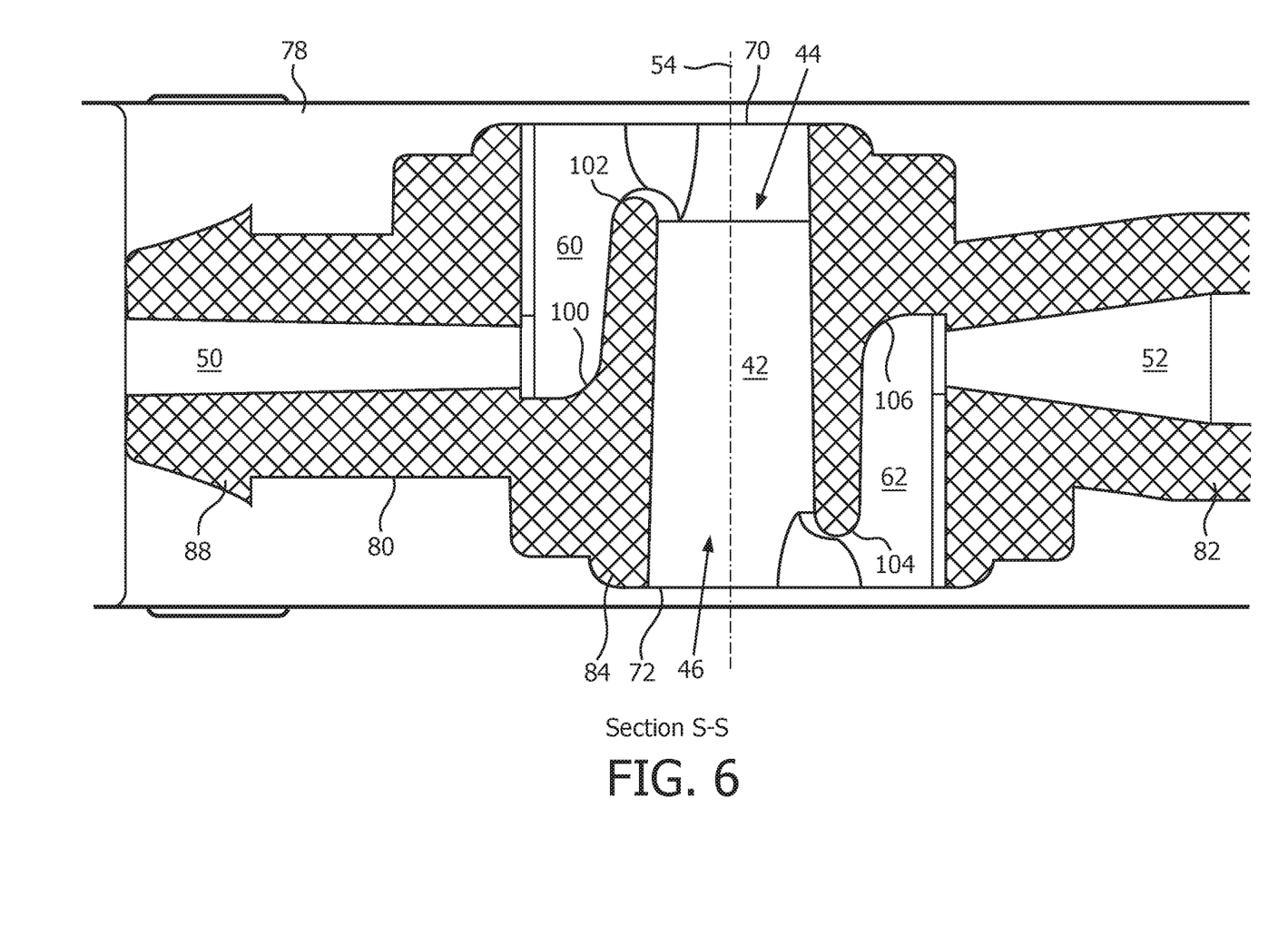
FIG. 6 shows an enlarged view of a portion of Section S-S of FIG. 5 centered on the sampling bore.

With reference to FIGS. 3(a)-(g) and 4-6, the illustrative sample cell 10 comprises a single-piece injection molded main body 40, for example made of an injection molded plastic. This single-piece injection molded main body 40 is shown in multiple views in FIGS. 3(a)-(g). FIG. 4 shows a side view of the sample cell 10 including the main body 40 and optical windows 70, 72, with a Section S-S line indicated. FIG. 5 shows the Section S-S along the line indicated in FIG. 4. FIG. 6 shows an enlarged view of Section S-S.

As seen in the sectional views of FIGS. 5 and 6, the single-piece injection molded main body 40 defines a gas flow path including (i) an optical sampling bore 42 with an inlet end 44 and an outlet end 46, (ii) a gas inlet lumen 50 connected with the inlet end 44 of the optical sampling bore 42, and (iii) a gas outlet lumen 52 connected with the outlet end 46 of the optical sampling bore 42. The optical sampling bore 42 defines an optical axis 54 along which the light source 20 (see FIG. 2) directs infrared probe light. In the illustrative main body 40, the gas inlet lumen 50 and the gas outlet lumen 52 are parallel, the gas inlet lumen 50 is orthogonal to the optical axis 54, and the gas outlet lumen 52 is also orthogonal to the optical axis 54. More particularly, in the illustrative embodiment the gas inlet lumen 50 and the gas outlet lumen 52 are coaxial as they share a common axis 55 as indicated in FIG. 5. Such a coaxial arrangement is advantageous in achieving compactness and can also reduce off-balance forces applied to the sample cell 10 when connecting components. To facilitate the illustrative arrangement, an inlet plenum 60 is disposed between the gas inlet lumen 50 and the inlet end 44 of the optical sampling bore 42, and similarly an outlet plenum 62 is disposed between the gas outlet lumen 52 and the outlet end 46 of the optical sampling bore 42.

As further seen in FIGS. 5 and 6, an inlet optical window 70 is attached to the single-piece injection molded main body 40 and covers the inlet end 44 of the optical sampling bore 42. Likewise, an outlet optical window 72 is attached to the single-piece injection molded main body 40 and covers the outlet end 46 of the optical sampling bore 42. In some embodiments, these optical windows 70, 72 seal the respective ends 44, 46 of the optical sampling bore 42. The optical windows 70, 72 may, for example, be biaxially oriented polypropylene films, although any window material may be used that is optically transparent for light output by the light source 20 and (if used to seal the optical sampling bore 42) provides sufficient sealing capacity. The optical windows 70, 72 may be secured to the main body 40 at the respective ends 44, 46 of the optical sampling bore 42 by any suitable adhering mechanism, such as ultrasonic welding, heat staking, laser welding, or so forth. In the illustrative sample cell 10, the inlet optical window 70 is oriented transverse to the optical axis 54, and the outlet optical window 72 is oriented transverse to the optical axis 54.

With particular reference to FIGS. 3(a)-(g), the single-piece injection molded main body 40 is shown in six orthogonal views in FIGS. 3(a)-(f) and in a perspective view in FIG. 3(g). The illustrative main body 40 includes a rectangular frame 78 that supports a tubular gas inlet 80 defining the gas inlet lumen 50 and a tubular gas outlet 82 defining the gas inlet lumen 52. A bore section 84 between the tubular gas inlet and outlet sections 80, 82 defines the optical sampling bore 42 and the plenums 60, 62. A cylindrical water filter hood 86 coaxially surrounds the tubular gas inlet 80 and provides additional support for the water trap filter 16. Optionally (or if required by applicable regulations), this filter hood 86 is illustrated with a standard ISO symbol for a gas inlet, as seen in FIGS. 3(a), (d), and (g). In the illustrative embodiment, the tubular gas inlet 80 has a nib 88, and the water trap filter 16 attaches to tubular gas inlet 80 via the nib 88, preferably with no adhesive being used to secure the water trap filter 16 on the tubular gas inlet 80. The tubular gas outlet 82 may, for example, be sized and shaped (e.g. with an illustrative conical tip) to mate into the internal air tubing 26 of the sampling bench 8 when the sample cell 10 is inserted into the mating receptacle 12 of the sampling bench 8 (see FIGS. 1 and 2). The illustrative main body 40 further includes finger grips 90, 92 on opposite sides of the single-piece injection molded main body 40 to facilitate the attachment and detachment, and a clasp, clip, or detent 94 on one clip 90 (as illustrated, or alternatively on both clips) to secure the sample cell 10 in the receptacle 12. It will be appreciated that if the sample cell is a permanent component of the sampling bench, rather than being detachable as illustrated, then the finger grips 90, 92 are suitably omitted and the clip 90 replaced by a permanent affixation mechanism.

With particular reference to FIG. 6, the illustrative sample cell 10 includes features which improve respired gas flow through the gas flow path 50, 60, 42, 62, 52. The improvements reduce flow turbulence and circulation at transitions that can lead to high background carbon dioxide readings, time latencies and/or memory effects. For example, if the respired gas tends to form a circular flow pattern at a relatively abrupt directional change, this circular flow pattern can hold carbon dioxide. Such an effect is of most significance when it traps or delays respired gas prior to entering the optical sampling bore 42. To suppress such effects, it is disclosed herein to incorporate at least one curved wall into the connection of the gas inlet lumen 50 and the inlet end 44 of the optical sampling bore 42. As best seen in FIG. 6, a concave curved wall 100 is arranged to re-direct gas flow exiting the gas inlet lumen 50 into the inlet plenum 60 disposed between the gas inlet lumen 50 and the inlet end 44 of the optical sampling bore 42. The concave curved wall 100 improves flow at the ~90° flow directional change. A convex curved wall 102 is arranged between the inlet plenum 60 and the inlet end 44 of the optical sampling bore 42 to suppress recirculation at this ~180° flow directional change.

Smooth flow out of the optical sampling bore 42 is also expected to reduce carbon dioxide background, memory effects or the like. To this end, a convex curved wall 104 is arranged between the outlet end 46 of the optical sampling bore 42 and the outlet plenum 62 to suppress recirculation at this ~180° flow directional change. A concave curved wall 106 is arranged to redirect flow from the outlet plenum 62 into the gas outlet lumen 52, which improves flow at this ~90° flow directional change.

A further improvement that is predicted to improve flow uniformity is to construct the optical sampling bore 42 as a tapered cylinder with the taper oriented such that the outlet end 46 of the optical sampling bore has a larger diameter than the inlet end 44 of the optical sampling bore 42. In some embodiments the taper is about 3°. A similar widening of the gas outlet lumen 52, as seen in FIG. 6, further improves flow by reducing likelihood of flow resistance at the gas outlet lumen 52 during high respired gas flow rates.

Figure 7:
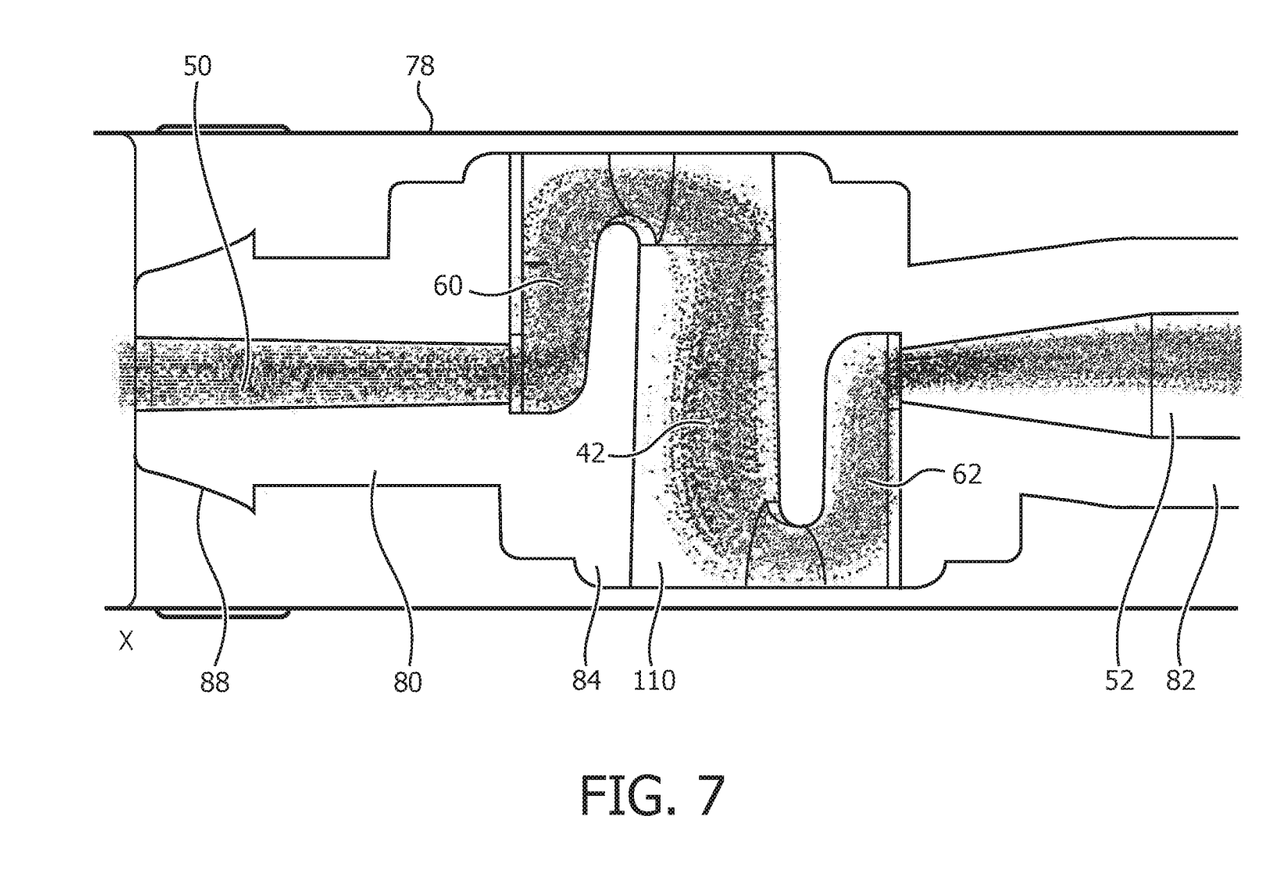
FIG. 7 shows a computer simulation of respiratory gas flow through the sample cell of FIGS. 1-6 viewed via the Section S-S view of FIG. 6.

With reference to FIG. 7, flow through the gas flow path 50, 60, 42, 62, 52 with the described turbulence-suppressing curved walls 100, 102, 104, 106 and flow resistance-reducing tapers of the optical sampling bore 42 and gas outlet lumen 52 was simulated, and the simulation results are shown in FIG. 7. It was found that the curved walls 100, 102 resulted in no observable turbulence for respired gas inflow into the optical sampling bore 42, and only minimal recirculation. Similarly, the curved walls 104, 106 resulted in no turbulence and only a small unswept corner 110 for the gas outflow, as seen at the outlet end 46 of the optical sampling bore 42. In transient simulations it was found that the carbon dioxide signal rise time was improved by 20% compared with an earlier design that did not include the curved walls 100, 102, 104, 106 and flow resistance-reducing tapers.

The disclosed sample cell 10 provides a synergistic combination of advantages. Construction as a single-piece injection molded main body 40 with only the optical windows 70, 72 and water trap filter 16 being separate components substantially reduces assembly complexity and cost when compared with existing approaches that require assembling multiple parts to form the main body, and also eliminates joints which are potential respired gas leakage paths. Use of the nib 88 to attach the water trap filter 16 further simplifies assembly as compared with existing approaches that employ glue to attach the water filter. The disclosed flow turbulence reducing features 100, 102, 104, 106 further improve performance of the disclosed sample cell 10.

Figure 8:
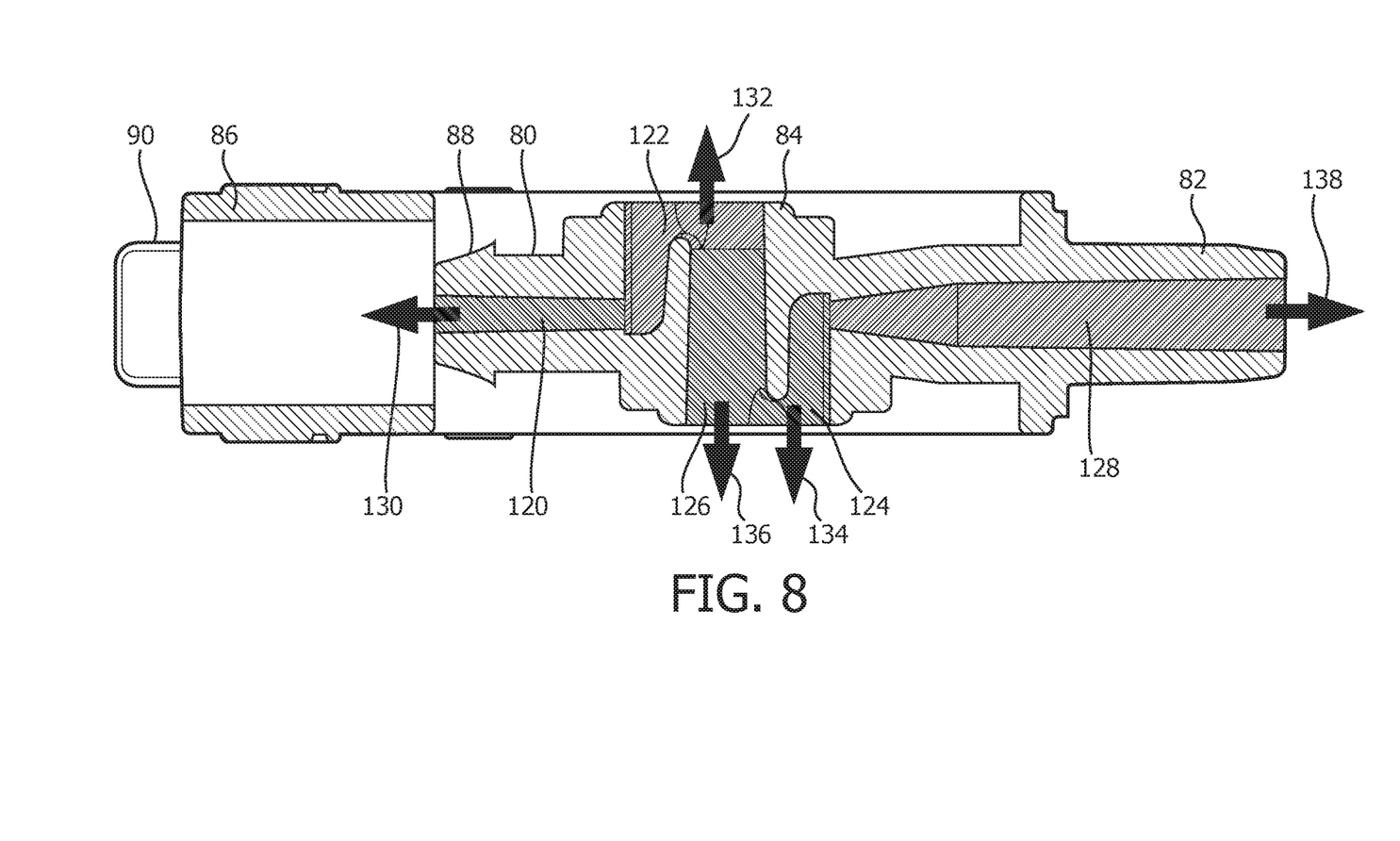
FIG. 8 shows the Section S-S of FIG. 5 with cross-hatching indicating pins for pulling the tool steel of the injection mold to define internal features.

With reference now to FIG. 8, manufacturing of the single-piece injection molded main body 40 is challenging, because the gas flow path 50, 60, 42, 62, 52 includes numerous sharp angles on the order of 90° or even 180°, and further includes the curved walls 100, 102, 104, 106 and flow resistance-reducing tapers. FIG. 8 illustrates a suitable combination of mold pins for use in the injection molding. The illustrative combination of mold pins includes an inlet lumen-defining mold pin 120 which is a straight cylindrical pin that defines the gas inlet lumen 50. A first complex mold pin 122 has two prongs and defines the inlet plenum 60 and the inlet end 44 of the optical sampling bore 42. The first complex mold pin 122 includes curve surfaces for defining the concave curved wall 100 and the convex curved wall 102 of the gas flow path. A second complex mold pin 124 has two prongs and defines the outlet plenum 62 and a small portion of the outlet end 46 of the optical sampling bore 42. The second complex mold pin 124 includes curved surfaces for defining the convex curved wall 104 and the concave curved wall 106. A bore-defining pin 126 defines most of the tapered optical sampling bore 42 including most of its outlet end 46. Finally, an outlet lumen-defining pin 128 defines the tapered gas outlet lumen 52.

The combination of mold pins 120, 122, 124, 126, 128 is designed to allow the mold pins to be pulled out, either during curing or after curing, in order to leave the defined lumens. The inlet lumen-defining mold pin 120 is withdrawn in the direction indicated by arrow 130 to remove it during or after the curing. The first complex mold pin 122 is withdrawn in the direction indicated by the arrow 132 to remove it during or after the curing. The second complex mold pin 124 is withdrawn in the direction indicated by the arrow 134 to remove it during or after the curing. The bore-defining pin 126 is then withdrawn in the same direction as indicated by the arrow 136. Since the second complex mold pin 124 "overlaps" the bore-defining pin 126, the order for pulling these mold pins is constrained: the second complex mold pin 124 is pulled first in direction 134 and then the bore-defining pin 126 is pulled in the same direction 136. Moreover, the bore-defining pin 126 can only be pulled in the direction 136 (and not, for example, in the opposite direction 132) due to the tapering of the bore-defining pin 126. The outlet lumen-defining pin 128 is pulled in the direction indicated by arrow 138, which again comports with the tapering of this mold pin.

The mold pins 120, 122, 124, 126, 128 are suitably made of steel, although other materials that can withstand the injection molding temperature and chemistry are also contemplated. Although not shown in FIG. 8, it will be appreciated that the junctions between the various mold pins may include mating features to minimize the potential for mold flashing at these junctions. It is also contemplated to secure some mold pins, such as the complex mold pins 122, 124, as part of the injection mold so that they are removed upon opening the injection mold.

Figure 9:
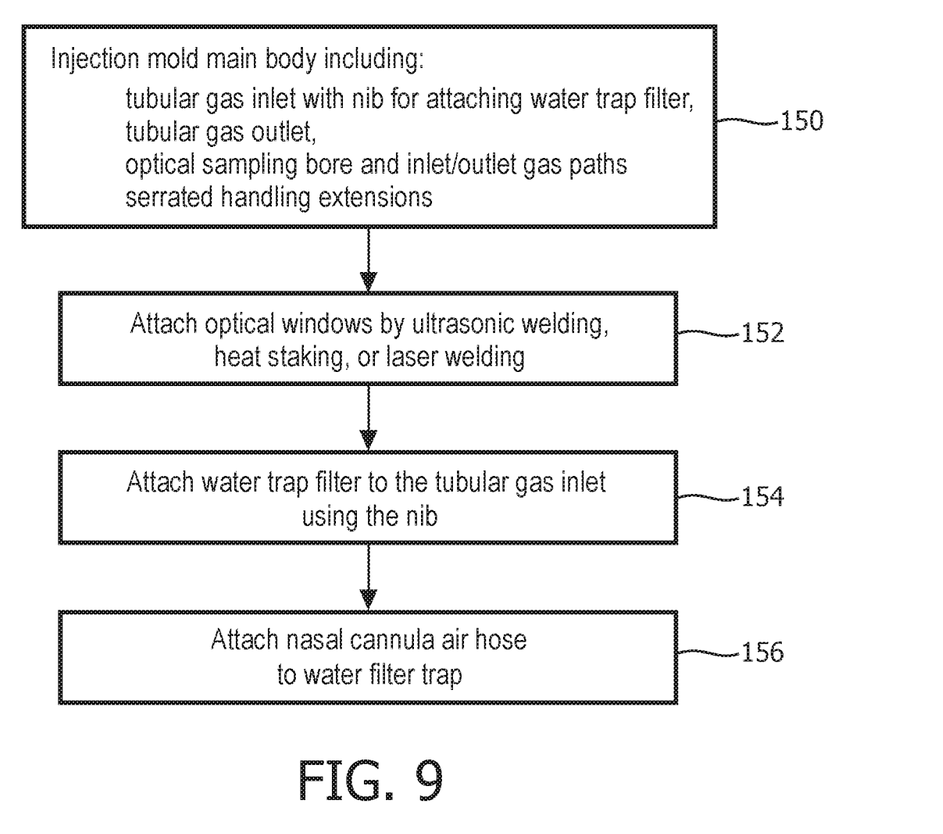
FIG. 9 shows a manufacturing flow chart for a suitable method of manufacturing the sample cell of FIGS. 1-8.

With reference to FIG. 9, a suitable process for manufacturing the sample cell 10 is described. In an operation 150 the single-piece injection molded main body 40 is formed by injection molding, e.g. using the mold pins described with reference to FIG. 8. Advantageously, this single step produces the main body 40 including the tubular gas inlet 80 with the nib 88 for attaching water trap filter 16, the tubular gas outlet 82, the optical sampling bore 42 and inlet and outlet gas paths 50, 52, 60, 62 preferably including the turbulence-reducing curved walls 100, 102, 104, 106 and tapers, and the handling extensions 90, 92 with serrations or other grip assists. In an operation 152, the inlet optical window 70 and the outlet optical window 72 are attached to the main body 10 using ultrasonic welding, heat staking, laser welding, or another suitable attachment method. In an operation 154 the water trap filter 16 is attached to the tubular gas inlet 80 using the nib 88 to retain the filter on the gas inlet. Preferably, the operation 154 does not include the use of glue or any other adhesive in securing the water trap filter 16. In an operation 156, the air hose 14 of a nasal cannula (or more generally, the air hose of a patient accessory) is attached to the water filter trap 16. (The order of the operations 154, 156 may be swapped). The result is the finished sidestream sampling consumable including the patient accessory, air hose 14, water trap filter 16, and disposable sampling accessory 10.

In the illustrative embodiments the single-piece injection molded main body 40 is employed. The skilled artisan readily appreciates that this component is structurally identifiable at least because it does not include seams or junctions due to its being injection molded as a single piece, and because it is made of a single material throughout, and because the gas flow path comprises segments that can be defined by mold pins, for example as described with reference to FIG. 8. These structural characteristics of the single-piece injection molded main body 40 have practical consequences such as elimination of potential gas leaks at seams or junctions between parts, and reduced manufacturing cost/complexity.

As previously noted, while the illustrative respired gas sensor is a carbon dioxide ($CO_2$) sensor, i.e. a capnography sensor, the disclosed sample cell 10 is readily employed in the context of other types of respired gas sensors, such as a respired oxygen sensor, where the improved manufacturability and/or reduced flow turbulence of the disclosed embodiments is/are readily seen as advantageous. It should be noted that while in the illustrative embodiments light propagation from the light source 20 to the light detector 22 is parallel with gas flow through the optical sampling bore 42 from the inlet end 44 to the outlet end 46, in other contemplated embodiments the gas flow may be in the opposite direction from the light propagation. Moreover, a non-parallel angle between the light propagation and the optical sampling bore axis 54 is contemplated. It is further noted that the inlet and outlet plenums 60, 62 can have shapes other than those of the illustrative embodiment. For example, the relatively sharp 90° turns at the concave curved walls 100, 106 and/or the relatively sharp 180° turns at the convex curved walls 102, 104 can be reduced by sloping these plenums to distribute the curvature over a longer gas flow distance, albeit at the cost of a sample cell with greater overall length and possibly more mold pins and/or more complex mold pin withdrawal configurations being needed to define such plenums. In another contemplated variant (not shown), if it is acceptable for gas inlet lumen 50 and the gas outlet lumen 52 to be non-coaxial, then the gas inlet lumen could directly connect with the inlet end 44 of the optical sampling bore 42 and likewise for the gas outlet lumen, so that the two plenums 60, 62 could be omitted entirely and a single ~90° convex wall placed at each connection to reduce turbulence.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A sample cell for a respired gas sensor, the sample cell comprising:
a single-piece injection molded main body defining a gas flow path including (i) an optical sampling bore with opposite inlet and outlet ends, (ii) a gas inlet lumen connected with the inlet end of the optical sampling bore, and (iii) a gas outlet lumen connected with the outlet end of the optical sampling bore;
an inlet optical window welded to the single-piece injection molded main body and covering the inlet end of the optical sampling bore; and
an outlet optical window welded to the single-piece injection molded main body and covering the outlet end of the optical sampling bore;
wherein the connection of the gas inlet lumen and the inlet end of the optical sampling bore includes:
a concave curved wall arranged to re-direct gas flow exiting the gas inlet lumen into an inlet plenum disposed between the gas inlet lumen and the inlet end of the optical sampling bore; and
a convex curved wall arranged between the inlet plenum and the inlet end of the optical sampling bore.

2. The sample cell of claim 1 wherein:
the inlet optical window seals the inlet end of the optical sampling bore; and
the outlet optical window seals the outlet end of the optical sampling bore.

3. The sample cell of claim 1 wherein:
the optical sampling bore defines an optical axis,
the inlet optical window is oriented transverse to the optical axis, and
the outlet optical window is oriented transverse to the optical axis.

4. The sample cell of claim 3 wherein:
the gas inlet lumen and the gas outlet lumen are parallel,
the gas inlet lumen is orthogonal to the optical axis, and
the gas outlet lumen is orthogonal to the optical axis.

5. The sample cell of claim 1 wherein the connection of the gas outlet lumen and the outlet end of the gas sampling bore includes:
a convex curved wall arranged between the outlet end of the optical sampling bore and an outlet plenum that connects with the gas outlet lumen; and
a concave curved wall arranged to re-direct gas flow exiting the outlet plenum into the gas outlet lumen.

6. The sample cell of claim 1 wherein the single-piece injection molded main body further includes finger grips on opposite sides of the single piece injection molded main body.

7. The sample cell of claim 6 wherein at least one of the finger grips comprises a protrusion of the single-piece injection molded main body having at least one of (i) an angle with respect to the single piece injection molded main body or (ii) a curvature arcing away from the single piece injection molded main body.

8. The sample cell of claim 6, wherein the finger grips are structured to facilitate a detachment of the sample cell from a sampling bench by an application of opposing forces applied to the finger grips.

9. The sample cell of claim 8, wherein the finger grips are further structured to at least one of (i) deactivate a locking mechanism, or (ii) actuate a release mechanism to facilitate detachment of the sample cell from the sampling bench by the application of opposing forces applied to the finger grips.

10. The sample cell of claim 1 wherein the single-piece injection molded main body further includes a tubular gas inlet defining the gas inlet lumen and having a nib, and the sample cell further comprises:
a water trap filter attached to the tubular gas inlet via the nib with no adhesive.

11. A sample cell for a respired gas sensor, the sample cell comprising:
a single-piece injection molded main body defining a gas flow path including (i) an optical sampling bore with opposite inlet and outlet ends, (ii) a gas inlet lumen connected with the inlet end of the optical sampling bore, and (iii) a gas outlet lumen connected with the outlet end of the optical sampling bore;
an inlet optical window attached to the single-piece injection molded main body and covering the inlet end of the optical sampling bore; and
an outlet optical window attached to the single-piece injection molded main body and covering the outlet end of the optical sampling bore;
wherein the optical sampling bore is a tapered cylinder with the taper oriented such that the outlet end of the optical sampling bore has a larger diameter than the inlet end of the optical sampling bore.

12. A respired gas carbon dioxide sensor comprising:
a sample cell as set forth in claim 1;
a light source arranged to inject light into the inlet end of the optical sampling bore of the sample cell; and
a light detector arranged at the outlet end of the optical sampling bore of the sample cell to detect the light from the light source after passing through the optical sampling bore of the sample cell.

13. The respired gas carbon dioxide sensor of claim 12 further comprising a pump connected to the gas outlet lumen of the sample cell to draw respired gas through the optical sampling bore of the sample cell; and
a sampling bench including the light source and the light detector and further including a sample cell receptacle configured to receive the sample cell as a detachable sample cell.

14. A sample cell for a respired gas sensor, the sample cell comprising:
a main body defining a gas flow path including (i) an optical sampling bore with opposite inlet and outlet ends, (ii) a gas inlet lumen connected with the inlet end of the optical sampling bore, and (iii) a gas outlet lumen connected with the outlet end of the optical sampling bore;
an inlet optical window attached to the main body and covering the inlet end of the optical sampling bore; and
an outlet optical window attached to the main body and covering the outlet end of the optical sampling bore;
wherein the connection of the gas inlet lumen and the inlet end of the optical sampling bore includes at least one curved wall; and
wherein the at least one curved wall of the connection of the gas inlet lumen and the inlet end of the optical sampling bore includes a convex curved wall arranged between the inlet end of the optical sampling bore and one of (i) the gas inlet lumen and (ii) an inlet plenum disposed between the gas inlet lumen and the inlet end of the optical sampling bore.

15. The sample cell of claim 14 wherein the at least one curved wall of the connection of the gas inlet lumen and the inlet end of the optical sampling bore further includes:

a concave curved wall arranged to re-direct gas flow exiting the gas inlet lumen into an inlet plenum disposed between the gas inlet lumen and the inlet end of the optical sampling bore.

* * * * *